(12) United States Patent
Isaacson et al.

(10) Patent No.: US 11,285,298 B2
(45) Date of Patent: Mar. 29, 2022

(54) MIDLINE CATHETER PLACEMENT DEVICE (71) Applicant: Becton, Dickinson and Company, Franklin Lakes, NJ (US)

(72) Inventors: Shawn Isaacson, Layton, UT (US); Weston Harding, Lehi, UT (US); Daniel Stipe, Raleigh, NC (US); Marc Weimer, South Jordan, UT (US); Charles Shermer, Raleigh, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 151 days.

(21) Appl. No.: 16/489,243

(22) PCT Filed: Mar. 16, 2018

(86) PCT No.: PCT/US2018/022780
§ 371 (c)(1),
(2) Date: Aug. 27, 2019

(87) PCT Pub. No.: WO2018/170349
PCT Pub. Date: Sep. 20, 2018

(65) Prior Publication Data
US 2020/0108230 A1    Apr. 9, 2020

Related U.S. Application Data

(60) Provisional application No. 62/472,984, filed on Mar. 17, 2017.

(51) Int. Cl.
*A61M 25/06* (2006.01)
(52) U.S. Cl.
CPC .... *A61M 25/0631* (2013.01); *A61M 25/0606* (2013.01); *A61M 25/0693* (2013.01)

(58) Field of Classification Search
CPC .......... A61M 25/0113; A61M 25/0606; A61M 25/0631; A61M 25/0618; A61M 25/0105; A61M 25/0693; A61M 25/09041
See application file for complete search history.

(56) References Cited

U.S. PATENT DOCUMENTS 4,944,728 A * 7/1990 Carrell .............. A61M 25/0606
604/110
4,957,489 A    9/1990 Cameron et al.
(Continued)

FOREIGN PATENT DOCUMENTS

CN    1817379 A    8/2006
CN    101208050 A    6/2008
(Continued)

OTHER PUBLICATIONS

Singapore Search Report dated Nov. 11, 2020, and Written Opinion dated Nov. 17, 2020, issued in the corresponding Patent Application No. 11201907683S.
(Continued)

*Primary Examiner* — Nathan R Price
*Assistant Examiner* — Mark A Igel
(74) *Attorney, Agent, or Firm* — Dickinson Wright PLLC (57) ABSTRACT

A catheter insertion device (10) is provided for positioning and inserting a catheter (14), particularly a midline catheter into a patient. The insertion device (10) includes an introducer needle (18) that extends from the distal end of the catheter during insertion. A manually operated actuator assembly (20) is movable with respect to a housing for deploying the catheter (14) over the distal end of the introducer needle (18). A step-wise movement of the actuator (20) advances the catheter (14) in stages over the
(Continued)

introducer needle (18). A shuttling or indexing mechanism (60, 76) advances the catheter and prevents retraction of the catheter once deployed.

23 Claims, 9 Drawing Sheets

(56) References Cited

U.S. PATENT DOCUMENTS

| | | | |
|---|---|---|---|
| 5,957,893 | A | 9/1999 | Luther et al. |
| 5,968,052 | A | 10/1999 | Sullivan, III et al. |
| 5,971,957 | A | 10/1999 | Luther et al. |
| 6,599,296 | B1 | 7/2003 | Gillick et al. |
| 8,932,258 | B2 | 1/2015 | Blanchard et al. |
| 2004/0019302 | A1 | 1/2004 | Williams et al. |
| 2009/0030380 | A1* | 1/2009 | Binmoeller ......... A61M 25/104 604/264 |
| 2011/0282285 | A1* | 11/2011 | Blanchard ......... A61M 25/0618 604/164.08 |
| 2017/0028171 | A1 | 2/2017 | Ishida |
| 2017/0216063 | A1* | 8/2017 | Bessho ..................... A61F 2/82 |

FOREIGN PATENT DOCUMENTS

| | | | |
|---|---|---|---|
| DE | 9000742 U1 | 4/1990 | |
| EP | 0827759 A2 | 3/1998 | |
| GB | 2355933 A * | 5/2001 | ........ A61M 25/0631 |
| GB | 2355933 A | 5/2001 | |
| JP | 2003-512903 A | 4/2003 | |
| JP | 2013-529111 A | 7/2013 | |
| WO | 2011143621 A1 | 11/2011 | |
| WO | 2015161294 A1 | 10/2015 | |
| WO | 2016178974 A1 | 11/2016 | |
| WO | 2016187063 A1 | 11/2016 | |

OTHER PUBLICATIONS

International Search Report dated Jun. 28, 2018, which issued in the corresponding PCT Patent Application No. PCT/US2018/022780.
Chinese Office Action dated Feb. 8, 2021, which issued in the corresponding Chinese Patent Application No. 201880018669.X, including English translation.
Extended European Search Report dated Jan. 22, 2021, which issued in the corresponding European Patent Application No. 18767821.4.

* cited by examiner

MIDLINE CATHETER PLACEMENT DEVICE

This application claims priority to U.S. provisional patent application Ser. No. 62/472,984, filed on Mar. 17, 2017, which is hereby incorporated by reference in its entirety.

FIELD OF THE INVENTION

The invention is in the field of catheter devices for delivering a medication or drug to a patient. Specifically the invention is directed to a catheter insertion device that can be operated in a manner to improve the efficiency of catheter insertion into a patient. The invention is particularly directed to a catheter insertion device that can be operated by one hand.

DESCRIPTION OF THE RELATED ART

Midline catheters are generally used for parenteral nutrition, IV fluid replacement and the administration of analgesics and antibiotics. Midline catheters are inserted at the bedside using sterile techniques and can remain in place for several weeks. The insertion (venipuncture) is performed above and below the antecubital fossa in the cephalic, basilica, or bronchial veins. The catheter tip is advances 3 inches to 8 inches with the tip terminating below the axilla and proximal central veins.

The potential advantages of a midline catheter are the reduced frequency of repeated venipunctures for labs/restarts, decreased incidence of catheter related infections, extended implant/indwell duration, improved clinical outcomes, patient satisfaction and associated cost savings. Placing the catheter tip in the larger diameter veins in the upper arm compared to the smaller veins provide improves drug delivery therapy and hemodilution. Midline catheters can be used for infusing contract media at higher flow rates that are typically done by CV catheters such as PICC applications.

Prior midline catheter devices typically include an integral guidewire. The guidewire is advanced through the lumen of the needle and into the vein after the needle accesses the vein. Often an ultrasonic probe or imaging device is used to locate the needle in the desired location. The catheter is then advanced over the guidewire into the vein. The needle and guidewire are then detached and separated from the catheter which remains in place in the vein.

The prior devices generally require the guidewire to be fully deployed by moving a sliding member into a locked/detent position. To advance the catheter, the clinician must put down the ultrasonic probe and use both hands to advance the catheter and complete the final steps of the procedure. This results in a loss of the visualization of the vein and the location of the catheter relative to the vein.

Catheter placement and advancement is dependent on holding the device in a stationary position with one hand while manipulating the catheter advancing mechanism in the other and without the use of the ultrasonic imaging to assist in proper placement of the catheter. Once the catheter is fully advanced, the clinician must re-position the ultrasonic probe to re-establish the image and confirm proper placement of the catheter. The operation requires a series of sequential steps with specialized training. The additional exchange of hand positions from the ultrasonic probe to the device and back to the probe adds complexity to the procedure and risk the success of the proper placement of the catheter.

Earlier methods for placing midline catheters were similar to the PICC placement. The Seldinger technique used a needle, dilator, guidewire, and sheath or catheter to access the vessel and ultimately place the catheter the vessel. The modified Seldinger technique coupled the dilator and sheath components together. Although providing some benefits, the potential risks remain, such as puncture of the back wall of the blood vessel, air embolism during component exchanges, contamination of components, bloodstream infection, excessive bleeding, blood splash contamination, needle stick injury and loss of cannulation access of loss of guidewire.

The accelerated Seldinger technique is a more recent method that combines the four components into a single unit. The resulted in a reduction in the number of component exchanges and open-to-air events, which reduce potential contamination and reduce the time needed to complete the procedure.

While the prior devices are generally suitable for the intended use, there is a continuing need for improved devices for controlling the penetration of a cannula for delivering a drug or medicament.

SUMMARY

The present invention is directed to a catheter insertion device for placement of an IV catheter in a selected location in the patient with reduced risk of movement of the device during insertion with respect to the selected location on the patient. In one embodiment, a midline catheter and a catheter insertion device are provided for insertion and placement of the catheter in the vein or artery of the patient. The catheter insertion device is able to place the catheter in a selected location and enable removal of an introducer needle with reduced risk of movement of catheter during the process. The catheter insertion device of the invention of the catheter does not require a guidewire to be inserted into the patient prior to inserting the catheter.

The midline catheter insertion device provides improved ergonomics and one-handed function. The catheter insertion device of the invention provides a one-handed advancement of the catheter while enabling the clinician to operate the ultrasonic probe to obtain images of the target blood vessel. The one-handed operation of the catheter insertion device enables holding the ultrasonic probe in one hand to provide visualization of the advancement of the catheter while holding the insertion device in the other hand.

The catheter insertion device in one embodiment includes a housing for supporting a catheter and an introducer needle for positioning the catheter in a selected location within the patient. The insertion device is able to slide the catheter forward over the stationary introducer needle to position the catheter in the vein or artery and then retract the introducer needle from the catheter. The insertion device avoids the need for a guidewire as in the prior devices.

The catheter insertion device in one embodiment includes a housing receiving a catheter hub having a catheter extending from one end of the hub and extending from a distal end of the housing. An introducer needle is fixed in the housing and extends through the catheter and extends from a distal end of the catheter for assisting in the insertion of the catheter into a patient. An actuator is operatively connected to the housing for moving the catheter forward to slide over the end of the introducer needle. The catheter and catheter hub can be released from the housing and the introducer needle retracted from the proximal end of the catheter and hub to separate the insertion device from the catheter after insertion.

The insertion device in one embodiment includes a housing having a sliding actuator that can be operated by the user to slide the actuator in a longitudinal direction with respect to a longitudinal dimension of the housing. A movable catheter and a fixed introducer needle are provided within the housing. The actuator is operatively connected to the catheter whereby sliding movement of the actuator in the longitudinal direction toward a distal end of the housing slides the catheter forward over the introducer needle. The actuator is configured to be able to move the catheter forward by incremental steps by sliding the actuator back to its original position and then sliding forward again. The actuator is comfortable and easy to use by the operator using one hand.

The catheter insertion device of the invention is configured to be held and operated by one hand and to advance the catheter over the introducer needle by a one-handed operation. The catheter insertion device is suitable for use while one hand of the user holds an ultrasonic probe for locating the catheter in a selected location and the other hand is able to hold and operate the catheter insertion device.

The catheter insertion device according to one embodiment includes a housing receiving a catheter, an introducer needle for the catheter and a shuttling or indexing assembly and mechanism for deploying the catheter with respect to the introducer needle. The shuttling mechanism is manually operated using one hand while holding the insertion device in a stable position with respect to the patient. The shuttling mechanism is able to deploy the catheter in a step-wise progression from a retracted position to an extended position. Once the catheter is deployed, the catheter and catheter hub can be released from the distal end of the housing so the introducer needle can be withdrawn from the catheter. A needle shield or cover can be deployed over the end of the withdrawn introducer needle to prevent accidental needle stick.

The various aspects and features of the invention are attained by providing a catheter insertion device comprising a housing, a catheter and catheter hub, an introducer needle and an actuator. The housing has a longitudinal axis with a distal end and a proximal end. The catheter hub and catheter are received in the housing where the catheter extends from the distal end of the housing. The introducer needle is fixed relative to the housing and is received in the catheter and projects from a distal end of the catheter. The actuator is coupled to the housing for advancing the catheter relative to the housing and the introducer needle by movement of the actuator.

The features of the invention are further attained by providing a catheter insertion device comprising a housing having a longitudinal axis with a distal end and a proximal end, a catheter and catheter hub, an introducer needle, and an actuator assembly. The catheter has a proximal end connected to a catheter hub and a distal end for insertion into a patient. The catheter and catheter hub are positioned in a longitudinal passage of the housing and are movable from a retracted position relative of the proximal end of the housing to a second position toward the distal end of the housing. The introducer needle is fixed in the housing and extends through a lumen of the catheter where the introducer needle projects from the distal end of the catheter when the catheter is in the first position. The actuator assembly in one embodiment includes a movable actuator coupled to the housing and is movable in a longitudinal direction relative to the housing and is operatively connected to the needle hub. The movable actuator is able to deploy the catheter relative to the introducer needle in a step-wise progression.

The features of the invention are further provided by an actuator for a catheter insertion device where the actuator includes a shuttling or indexing mechanism to advance the catheter forward from the distal end of the housing. The catheter and catheter hub can be released from the housing and the introducer needle can be withdrawn and discarded.

The various features of the invention are further attained by providing a method of inserting a catheter into a patient by use of the catheter insertion device. The catheter with the introducer needle projecting from a distal end of the catheter is inserted into the patient in the desired location. An actuator on the insertion device is manually manipulated to slide the catheter in the distal direction relative to the device and the introducer needle to position the distal end of the catheter in the patient with the distal end of the introducer needle positioned within the catheter. The catheter and catheter hub are separated from the housing of the device and the introducer needle retracted from the catheter.

It will be understood that each of the preferred or optional features of the various embodiments may be combined with other features and features described in combination with one or more particular features may also be combined with one or more other features of the other embodiments.

These and other features of the invention will become apparent from the following detailed description of the invention, which in conjunction with the drawings disclose various embodiments of the invention.

BRIEF DESCRIPTION OF THE DRAWINGS

The following is a brief description of the drawings in which.

DETAILED DESCRIPTION OF THE INVENTION

A catheter insertion device is provided for positioning a catheter in a patient for delivering a medication or other substance to a patient. The terms "needle" and "cannula" can be used herein interchangeably to refer to a member having a sharpened or beveled end for insertion into an injection site on a subject. In one embodiment, the needle can be a thin hollow tubular member. The distal end refers to the end of the device toward the patient and the proximal end refers to the opposite end away from the patient. As used herein, the "distal" direction is in the direction toward the patient and injection site, and the "proximal" direction is the opposite direction. "Axial" means along or parallel to the longitudinal axis of the needle and the "radial" direction is a direction perpendicular to the axial direction. The forward direction is the direction toward the distal end of the device.

The invention may assume various alternative variations, except where expressly specified to the contrary. It is also to be understood that the specific devices illustrated in the attached drawings, and described in the following specification, are exemplary embodiments of the invention. Specific dimensions and other physical characteristics related to the embodiments disclosed herein are not to be considered as limiting. The embodiments are not intended to be mutually exclusive so that the features of one embodiment can be combined with other embodiments as long as they do not contradict each other.

The present embodiments are directed to a catheter insertion device for inserting a positioning a catheter in a patient. The embodiments are particularly suitable for use with midline catheter that can be used in conjunction with an ultrasonic imaging device for assisting in positioning the device in a selected location and selected depth in the patient. The catheter can be a commonly used length and a commonly used diameter. The catheter insertion device 10 of the invention basically includes a main body or housing 12, a catheter 14 having a catheter hub 16, an introducer needle 18, and an actuator assembly 20. Actuator assembly 20 forms a shuttling or indexing assembly and mechanism to index and advance the catheter 14 over the end of the needle 18.

Figure 1:
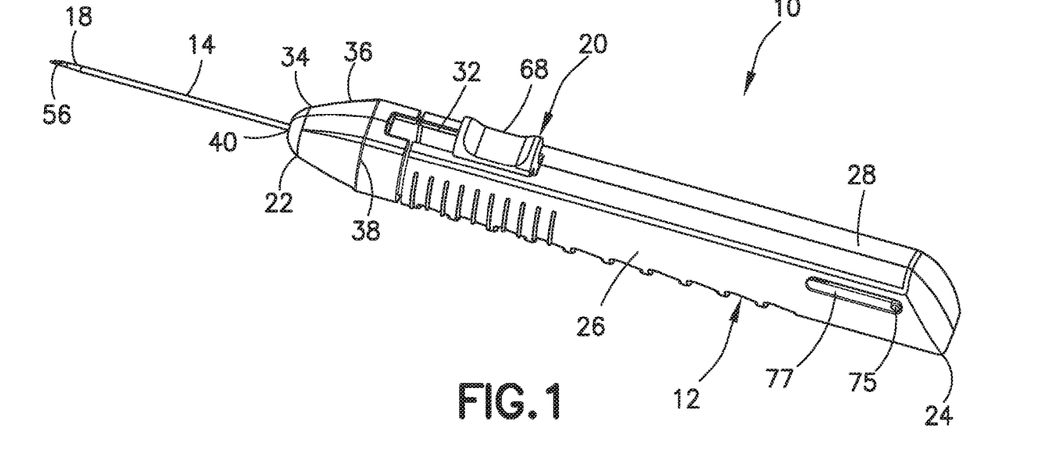
FIG. 1 is a perspective view of the catheter insertion device showing the actuator in the starting position.
Figure 2:
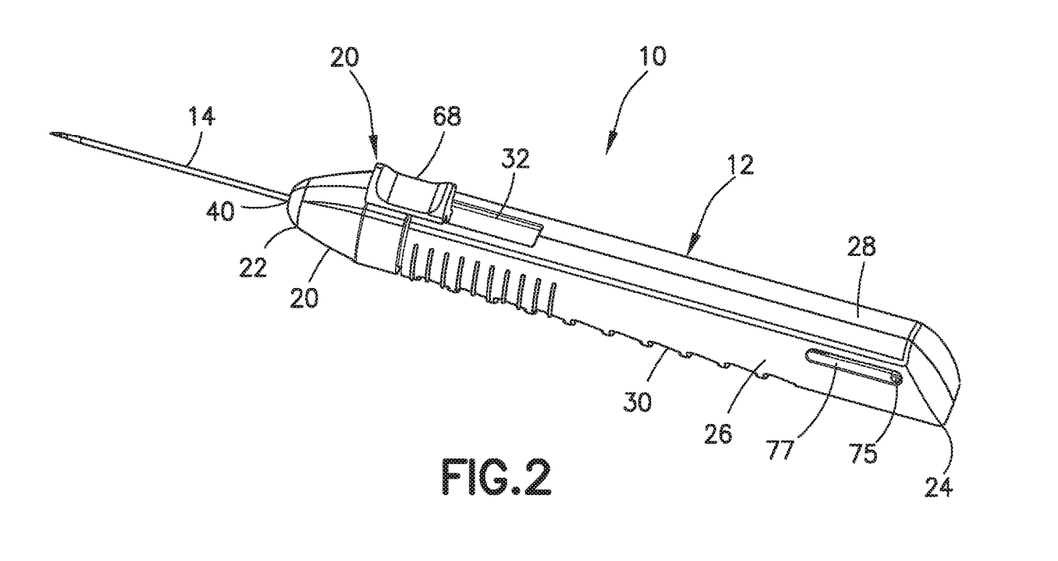
FIG. 2 is a perspective view of the catheter insertion device of FIG. 1 showing actuator in the forward actuated position.
Figure 3:
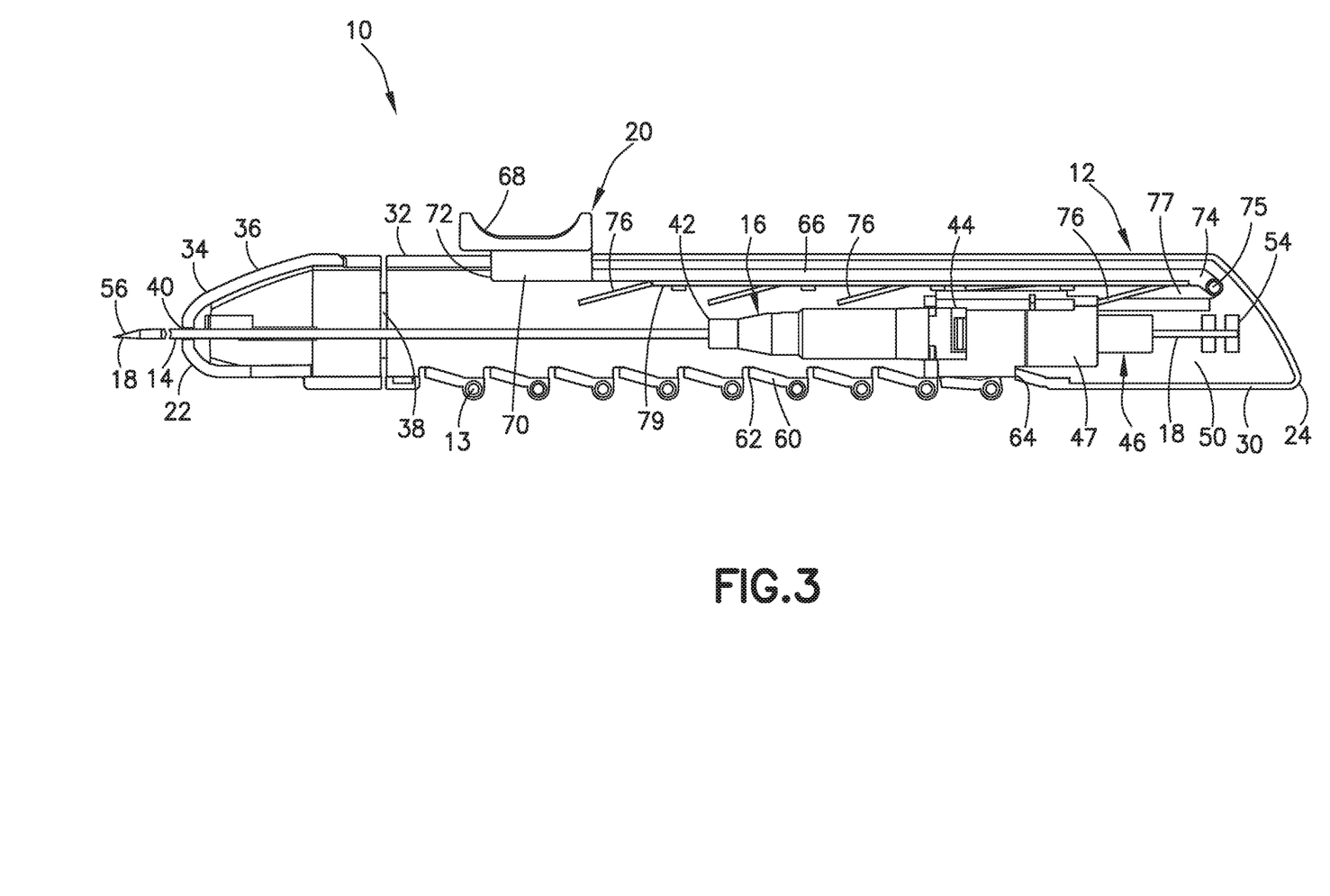
FIG. 3 is a side view of one housing half of the catheter insertion device of FIG. 1 showing the catheter and hub in the original starting position with the introducer needle extending from the distal end of the catheter.

Referring to FIGS. 1 and 2, housing 12 of the insertion device 10 has a longitudinal dimension with a distal end 22 and a proximal end 24. In the embodiment shown, the housing 12 is formed from two housing halves that are joined together by a suitable attachment mechanism. The halves are aligned by pins protruding from a first half and corresponding recesses 13 on the other half as shown in FIG. 3. The housing 12 has a dimension for supporting the introducer needle 18 and catheter 14 during use and to enable the user to manipulate the device in positioning the catheter. The housing has a cavity 50 forming a longitudinal passage. In the embodiment shown the housing 12 has curved side walls 26, a flat top wall 28 and a flat bottom wall 30. The flat bottom wall is generally provided to allow the device to be placed on a flat surface in a stable position with reduced risk of falling off the surface. The shape of the device can vary depending on the particular use to provide comfortable and convenient use by the operator.

Figure 6:
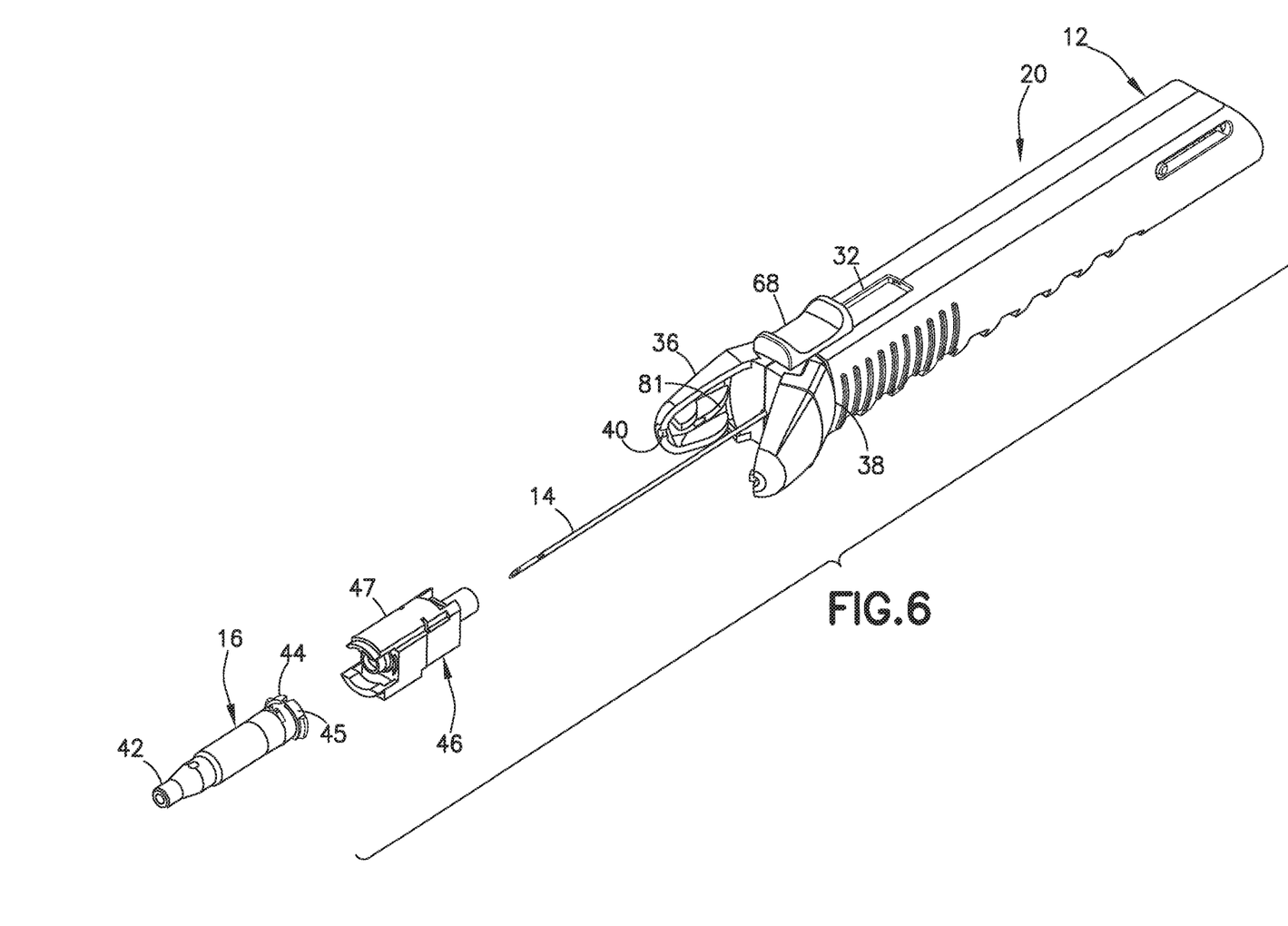
FIG. 6 is a perspective exploded view showing the catheter and needle shield separated from the housing.

In the embodiment shown, an elongated opening 32 is formed in the top wall 28 for receiving the actuator assembly 20. A tip 34 having converging sides defines the distal end 22 of the housing. As shown in FIG. 6, two hinged walls 36 of tip 34 are pivotally connected to the walls 26 by a respective hinge 38 to access the interior of the housing and allow removal of the catheter from the housing as discussed in further detail below. An outlet opening 40 in tip 34 enables the catheter and introducer needle to extend from the distal end of the housing during use. The converging surfaces of tip 34 enable the device to be positioned at a low angle with respect to the skin of the patient to assist in inserting the catheter 14 and introducer needle 18 into the patient with reduced risk of kinking or folding of the catheter 14.

Referring to FIGS. 3, 7 and 8-12, catheter 14 is shown extending from catheter hub 16 that fits and slides within the housing 12. Hub 16 has a distal end 42 connected to catheter 14 and a proximal end 44 having a collar 45. Proximal end 44 is coupled to a body 47 of a needle safety assembly 46. The body 47 is a movable body or a body that can slide within the housing 12 and can be referred to herein interchangeably as the body 47. In the embodiment shown in FIG. 6, hub 16 has the radially extending collar 45 at the proximal end for coupling with a luer fitting during use. A flexible seal 48 shown in FIG. 7 forming a valve is provided in hub 16 at the distal end for closing the end and preventing leakage when the introducer needle is removed from the hub. The flexible seal 48 can be a rubber member or septum with a slit for allowing the introducer needle 18 to pass through and close when removed. A standard luer fitting can be coupled to the proximal end of hub 16 such that an actuator opens the valve to allow delivery of the substance or withdrawing fluid from the patient.

Catheter 14 can be a commonly used catheter and have a dimension commonly used in the art. By way of example, catheter can be 18 gauge or less. 20 gauge, 22 gauge, 24 gauge or 26 gauge. In one embodiment, the catheter can have a length of about 3 inches although other lengths can be used.

Figure 7:
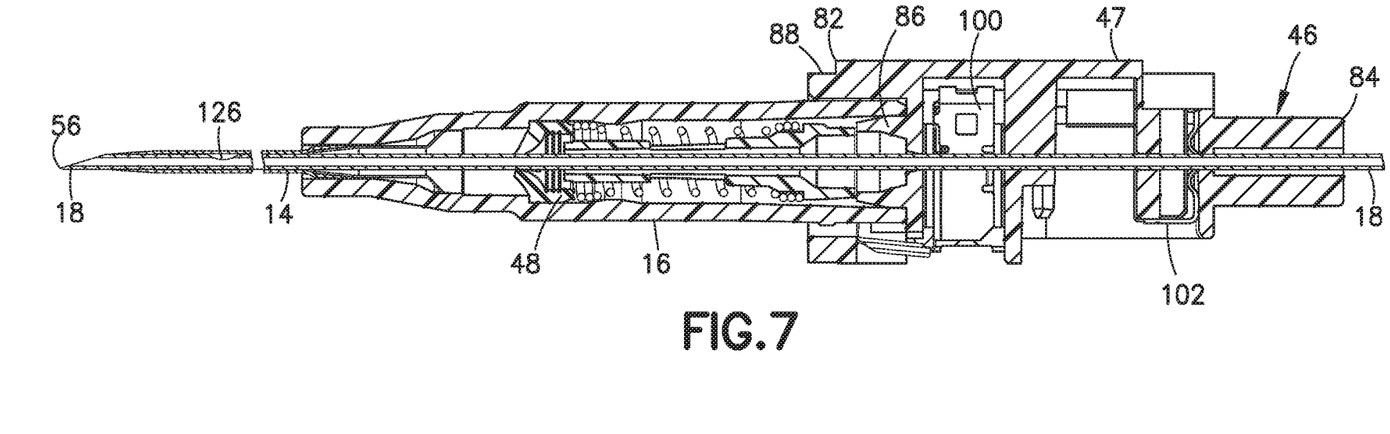
FIG. 7 is a side view in cross section of the safety assembly of the needle insertion device in one embodiment.

The introducer needle 18 in the embodiment shown in FIGS. 3-6 is hollow and has a proximal end 52 fixed within a cavity 50 of housing 12 by a post 54 or other support and a distal end 56 shown in FIGS. 3 and 7 extending from the distal end of housing through the opening 40. As shown in FIG. 1, introducer needle 18 extends from the distal end of the housing a distance to enable proper insertion into the patient. The distal end of the catheter 14 in the initial position is spaced from the distal end of the introducer needle 18 toward the proximal end so that the introducer needle 18 extends past the distal end of the catheter 14 as shown in FIG. 7. The distal end 56 of introducer needle 18 in the embodiment shown has a beveled and sharpened tip as known in the art for piercing the skin and inserting into the patient.

The body 47 of safety assembly 46 in the embodiment shown is received in the longitudinal passage of the cavity 50 of housing 12 and is coupled to hub 16 during use and separated after insertion of the catheter 14 in the patient. In the embodiment shown in FIGS. 3-5, safety assembly 46 defines a shield to cover the distal end of introducer needle after use. Safety assembly 46 and body 47 are able to move or slide within the housing 12 during deployment of catheter 14 with respect to the introducer needle 18.

Figure 4:
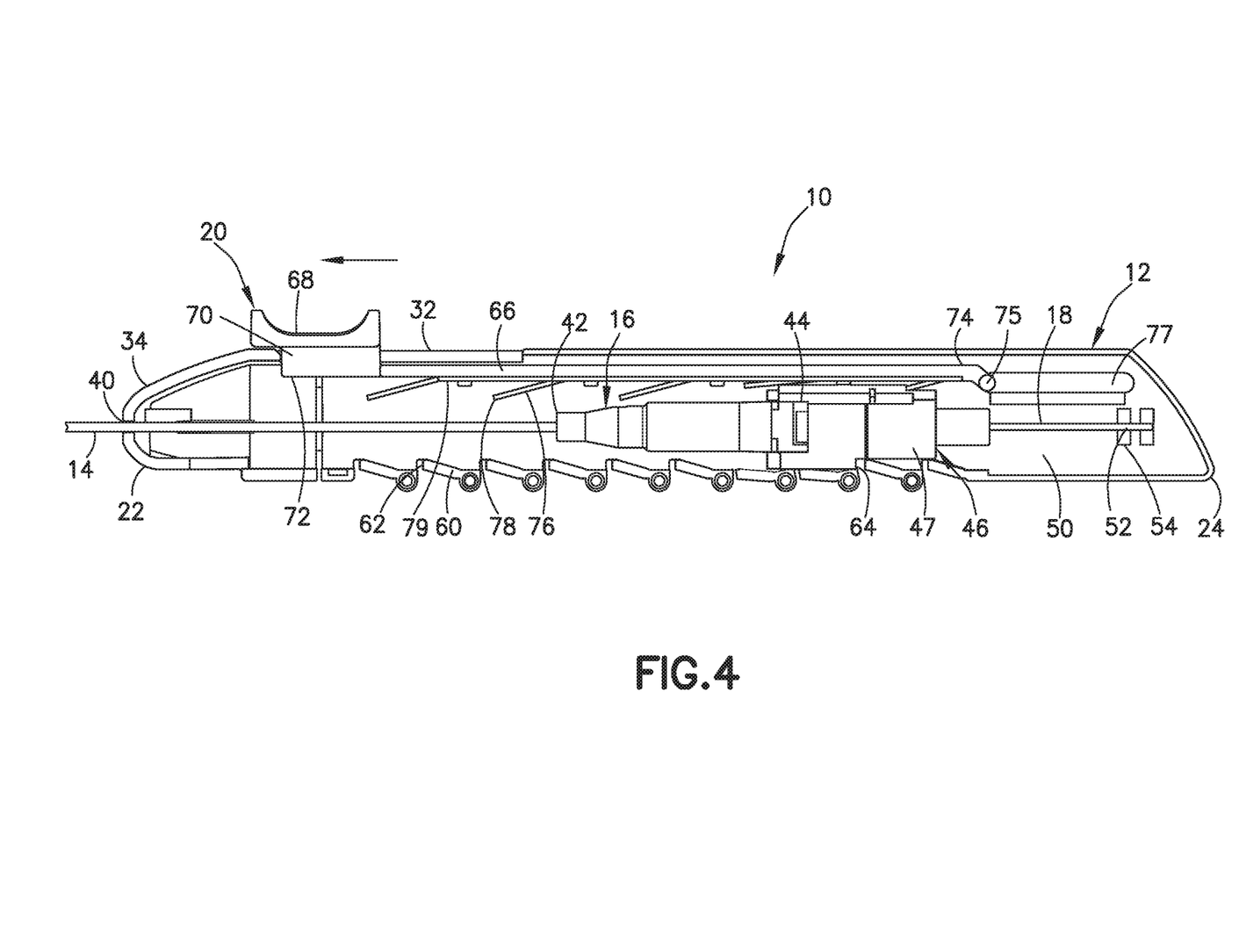
FIG. 4 is a side view of the housing half of the catheter insertion device of FIG. 3 showing the actuator moved to the actuated position and the catheter advancing within the housing.
Figure 5:
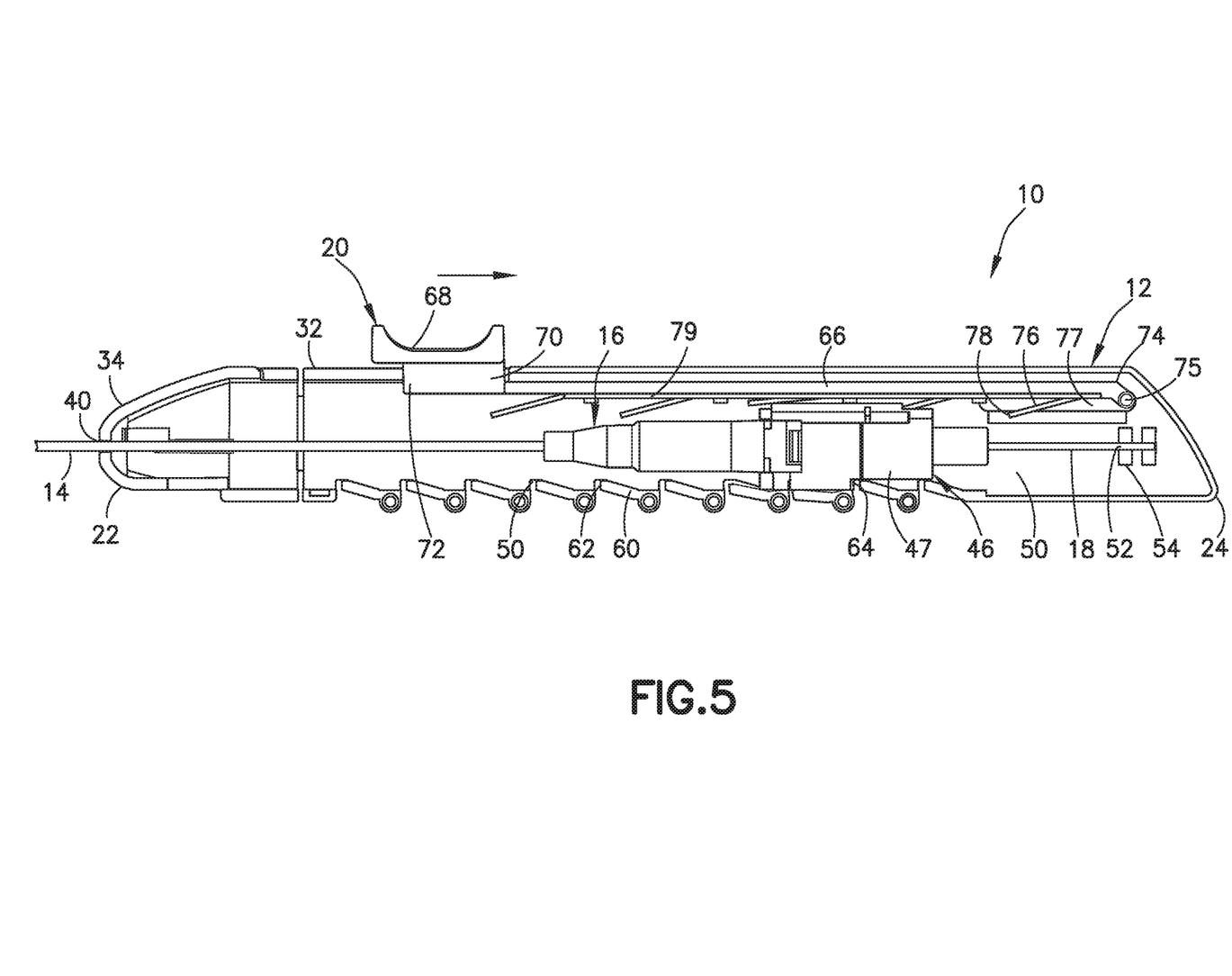
FIG. 5 is a side view of the catheter insertion device of FIG. 3 showing the actuator moved back to the original position while the catheter remains in the advanced position.

In the embodiment shown, wall 30 of housing 12 includes at least one tab 60 that allows safety assembly 46 and the catheter to move or slide toward the distal end 22 of housing 12 and to prevent the safety assembly 46 from moving or sliding back toward the proximal end 24 of housing 12. In one embodiment, a plurality of tabs 60 as shown in FIGS. 3-5 are provided where each tab is formed at an incline and projects into the open center of the housing and projects toward the distal end 22 of housing 12. The tabs 60 in one embodiment are integrally formed with the wall 30. In the embodiment shown, tabs 60 are biased inwardly toward the center axis of the housing 12 and can flex or deform by the forward movement of the body 47 of safety assembly 46 over the tabs and return to the original position to assist sliding toward the proximal end of housing 12 and resisting moving back toward the proximal end of housing 12. In one embodiment, the flexible tabs 60 allow the body 47 of safety assembly 46 to slide over the body 47 of safety assembly 46. In other embodiments, tabs 60 can be rigid. The housing 12 can be made of a molded plastic material to provide resilient properties to the tabs 60 for bending and returning to the original position.

In one embodiment of the invention, a series or plurality of tabs 60 are provided on the wall 30 and angled at an incline toward the distal end of the housing as shown in FIGS. 3-5. The tabs 60 are spaced apart a substantially uniform distance along the length of the housing to define a length of travel of the body 47 of the safety assembly 46 and catheter 14 within housing 12. The spaced apart tabs 60 form part of a ratcheting, shuttling or indexing assembly or mechanism for advancing the catheter 14 from a first starting position shown in FIG. 3 to a second extended position shown in FIG. 5 toward the distal end of housing 12. The tabs 60 have a distal end 62 that engage a surface 64 on the safety assembly 46 that prevents the body 47 of safety assembly 46 from moving or sliding back toward the proximal end of the housing. The body 47 is able to slide over the tabs 60 by the forward movement of the body where the tabs spring back to the original position to resist movement of the body toward the proximal end of the housing.

Actuating assembly 20 is provided in the housing 12 to engage the body 47 of safety assembly 46 to advance the body 47 and catheter 14 toward the distal end 22 of housing 12 after the introducer needle 18 and the catheter 14 are positioned in the selected location in the patient. The actuating assembly 20 forms a ratcheting, shuttling or indexing assembly for advancing or indexing the catheter relative to the needle 18. In the embodiment shown, actuating assembly 20 includes an actuator body 66 positioned within the housing 12 between the wall 28 and the body 47 of safety assembly 46. A finger operated button 68 is connected to the actuator body 66 by a connecting member 70 that extends through and slides within the elongated opening 32 in the wall 28. Button 68 is oriented on the outer surface of top wall 28 for access by the operator.

As shown in the drawings, the actuator body 66 has a longitudinal length complementing the longitudinal length of housing 12 to slide and reciprocate within the cavity of the housing 12. Actuator body 66 has a substantially flat, planar configuration in the embodiment shown with a proximal end 72 and a distal end 74. The distal end 74 has a guide pin 75 that slides in a slot 77 in the walls 26. In the embodiment shown the button 68 is connected to the distal end 74 of actuator body 66 for ease of use by the operator. In other embodiments, the button 68 can be located at other suitable locations on the length of the actuator body 66 and the housing 12.

The actuator body 66 of actuator assembly 20 includes at least one and typically a plurality of tabs 76 for engaging the body 47 to advance the body 47 and catheter 14 in a step-wise manner toward the distal end of the housing by the reciprocating movement of the body 47. The tabs 76 form a ratcheting mechanism for advancing and indexing the body 47 toward the distal end of the housing. The actuator body can be made of a suitable plastic material. In the embodiment shown, the tabs are formed with a base plate 79 that is attached to a face of the actuator body 66. In one embodiment, the base plate 79 and tabs 76 can be made of metal or plastic. The tabs 76 can be integrally formed with the actuator body 66 in other embodiments. In one embodiment, the actuator body 66 can be made of plastic.

In the embodiment shown, the tabs 76 are formed at an incline in a manner to complement tabs 60. Tabs 76 extend from the actuator body 66 and project toward the center axis of the housing 12 and project toward the distal end 22 of the housing 12. Tabs 76 in the illustrated embodiment are generally flexible to be able to slide over the body 47 of the safety assembly 46. Distal ends 78 of the tabs 76 are biased inwardly toward the center axis of the housing and spring back to the original orientation after sliding over the body 47 of safety assembly 46. The plurality of tabs 76 form the ratcheting, shuttling and indexing mechanism and are oriented for moving the catheter 14 and safety assembly 46 toward the distal end of the housing. In other embodiments, tabs 60 can be fabricated as one or more components. Button 68 and actuator 66 can also be made as one or more components.

In use, the distal end of the 56 of the introducer needle 18 extends from the catheter 14 and the catheter 14 is positioned in a starting position toward the proximal end of the housing as shown in FIG. 3. The introducer needle 18 and the catheter 14 are inserted into the selected position in the patient for the intended use. The insertion device 10 is configured for ease of use by one hand to pierce the skin and position the catheter and introducer needle in the patient while freeing the user's other hand for holding other devices such as an ultrasonic imaging device commonly used to ensure proper placement of the catheter in the patient. The button 68 of the actuator assembly 20 is initially in the retracted position shown in FIG. 3. Using one finger or thumb, the user can slide the button 68 forward to the second position shown in FIG. 4. The tab 76 toward the proximal end of the actuator body 66 engages the body 47 and slides the body 47 and the catheter 14 forward a distance corresponding to the distance of travel of the actuator button. The tabs 60 on the bottom wall 30 of the housing 12 are positioned to complement the spacing and location of the tabs 76 so that the forward movement of the body 47 toward the distal end of the housing engage the respective tab 60 to retain the body 47 in the advanced position and prevent the body 47 from sliding back toward the proximal end of the housing. The advancing movement of the body 47 advances the catheter forward over the fixed introducer needle 18.

The button 68 can then slide back toward the proximal end of the housing 12 where the tabs 76 slide over the body 47 to engage a contact point on the body 47 as shown in FIG. 5. The button 68 can slide by manual manipulation by the user or can slide by a spring member in the housing between the housing and the body. The button 68 can then slide forward again to slide the body 47 and catheter 14 forward to slide the distal end of the catheter past the distal end of the introducer needle. The sliding movement of the button can be repeated in a step-wise manner to advance the catheter to the extended position relative to the introducer needle 18 and housing 12. In one embodiment of the invention, the button 68 slides by manual manipulation by the user in a repeated sliding movement forward and backward to push the catheter, catheter hub and safety assembly in the distal direction toward the patient by each forward stroke of the button and actuator body. At the completion of each forward stroke, the button is pulled back and the next tab of the actuator body is readied for the next forward stroke. With each forward stroke, the tabs on the housing engage the body 47 to prevent moving to the proximal end of the housing.

Once body 47 and catheter hub 16 are advanced to the forward position at distal end 22 of housing 12, hinged walls 36 are pivoted to the open position shown in FIG. 5 to release catheter hub 16 and body 47 and safety assembly 46 from housing 12. The catheter hub 16 is advanced to contact cam surfaces 81 on the inner surface of the doors 36 to push the doors 36 open. Housing 12 can be pulled away from catheter hub 16 to withdraw introducer needle 18 from catheter 14. Body 47 slides over distal end 56 of introducer needle 18 to enclose the sharp tip and prevent an accidental needle stick. Catheter hub 16 is released and separated from safety assembly 46 when body 47 of safety assembly 46 is actuated by the withdrawing of introducer needle 18. Housing 12, with the attached introducer needle 18 and body 47 are discarded in a sharps container. Seal 48 forms a valve that closes to control blood backflow and to allow attachment of an extension set or other device.

The actuator assembly 20 as shown is one example of a mechanism that can be used to advance the catheter over the introducer needle. In other embodiments, various mechanisms can be used that are able advance the catheter relative to the needle. In one exemplary embodiment, a wheel or rotatable member can be mounted in the housing to engage the body and advance the catheter hub. The wheel can be rotated manually by the thumb or finger of the user to cause the body and catheter to slide toward the distal end of the housing over the end of the introducer needle.

In various embodiments of the invention, the actuator assembly 20 can have other suitable constructions and mechanisms that are able to advance the catheter over the end of the needle by a single operation or by a sequence of repeated operations by the user. In the embodiment shown, the tabs are flexible and formed on the inner surfaces of the opposing walls of the housing that engage the body of the safety assembly although other arrangements of parts and components can be used effectively. In one alternative embodiment, tabs, detents or other members can be formed on or attached to the body of the safety mechanism that engage complementing tabs, detents or members on the actuator body and/or housing to provide the advancement of the catheter over the end to the needle. An inner surface of the housing can be formed with one or more detents, ridges, recesses or other structure that engage the detent or member on the safety assembly. For example, a detent can be formed on one or more surfaces of the body of the safety assembly that engage a complementing detent or recess in the housing that enable the safety assembly and catheter to travel in a direction toward the distal end of the housing to slide the catheter over the end of the needle. A detent or other member can also be formed on the body of the safety assembly to engage a complementing member on a movable actuator that is able to slide or move the safety assembly toward the distal end of the housing in a manner that will advance the catheter over the end of the needle.

Body 47 defines the safety needle assembly 46 which is a passive needle shield that can be deployed to cover the tip of the introducer needle 18. Safety needle assembly 46 is similar to devices disclosed in WO2015/161296 and WO2015/161294 which are hereby incorporated by reference in their entirety.

FIGS. 7-12 show one embodiment where the safety assembly 46 includes body 47 with a proximal end 82 and a distal end 84. In the embodiment shown, distal end 84 has an inner protrusion 86 and an outer ring 88 forming an annular ring for coupling with the proximal end 44 of catheter hub 16 as shown in FIG. 7. Proximal end 52 of introducer needle 18 is fixed to proximal end 24 of housing 12 and extends through a longitudinal passage in body 47 and through seal 48 and catheter 14.

The proximal end of catheter hub has an outer diameter that is greater than the portion of the diameter of the hub adjacent to the collar 45. The collar extends around a portion of the hub and is formed with an opening.

Figure 8:
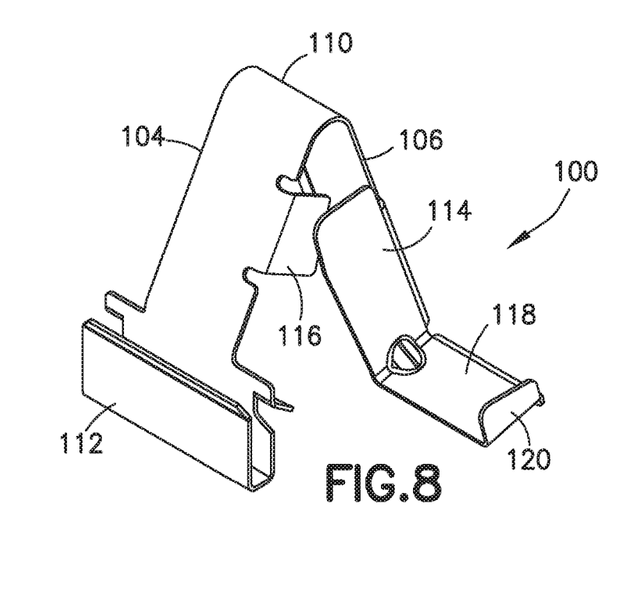
FIG. 8 is a perspective view of the clip of the safety assembly.
Figure 9:
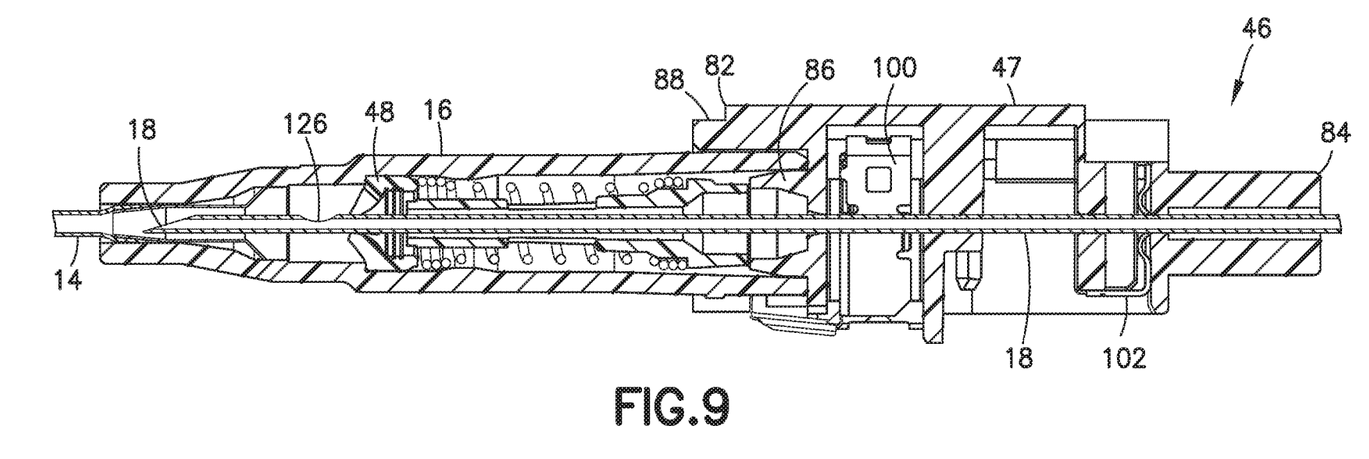
FIG. 9 is a side view in cross section showing the introducer needle partially withdrawn.
Figure 10:
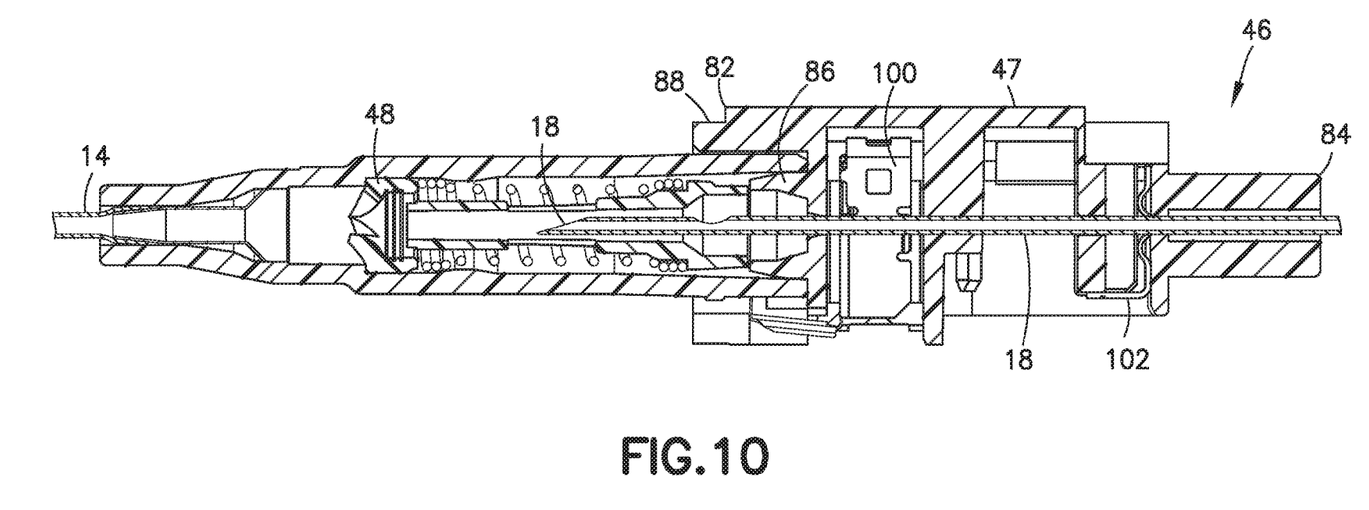
FIG. 10 is a side view in cross section showing the introducer needle withdrawn from the blood control valve.
Figure 11:
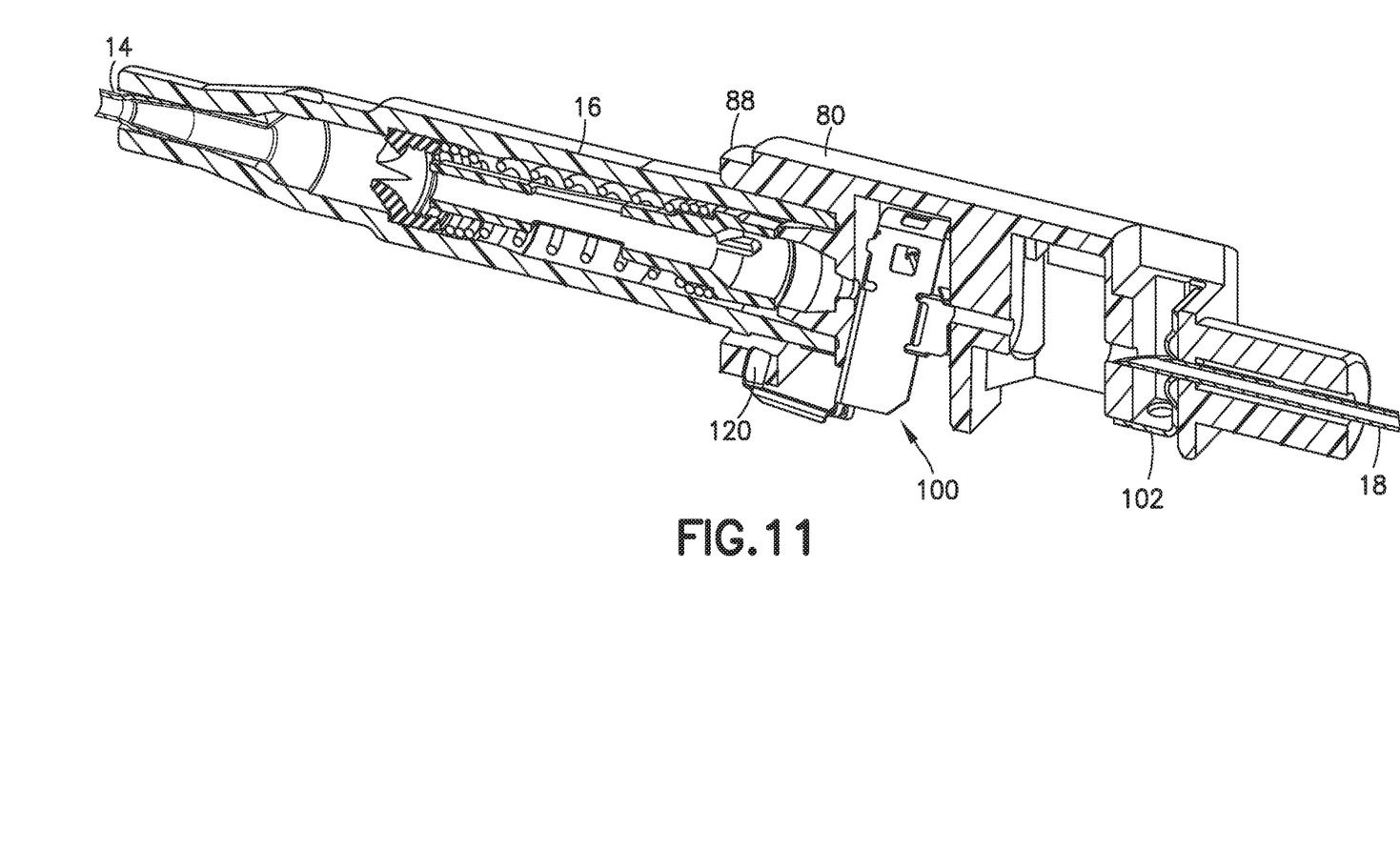
FIG. 11 is perspective view in cross section showing the introducer needle withdrawn to activate the spring clip.
Figure 12:
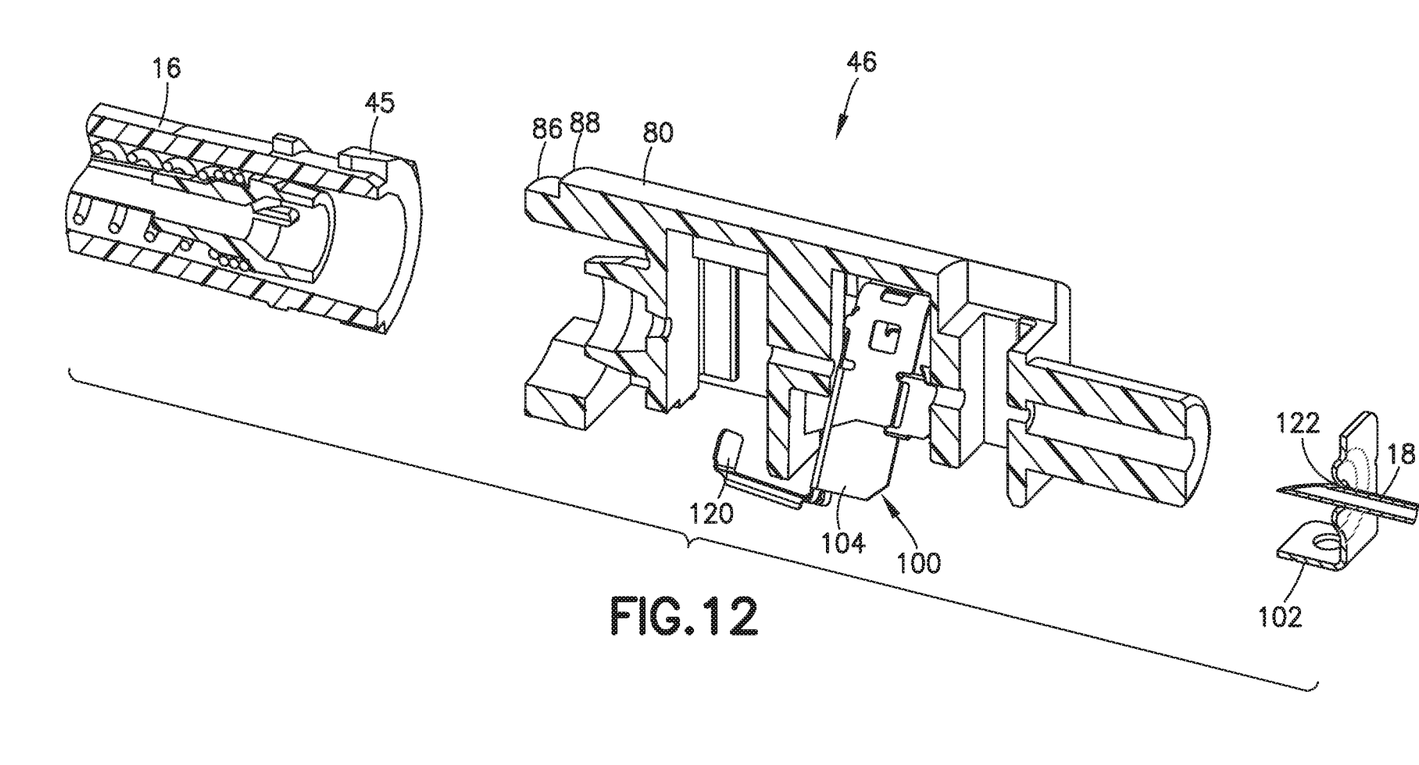
FIG. 12 is a perspective view in cross section showing the catheter hub separated from the safety assembly.

The safety assembly 46 includes a resilient clip 100 and a washer 102. The body 47 of the assembly has an opening to receive the introducer needle 18. The distal end of the body 47 is configured for coupling with the proximal end of the catheter hub 16. The resilient clip 100 as shown in FIG. 8 has a substantially V-shape having a first leg 104 and a second leg 106 connected by a hinged section 110. In the embodiment shown, the first leg 104 includes a spade 112 having an angled portion for coupling to the body 47. A first flag 114 extends from the second leg 106 toward the first leg 104 and a second flag 116 extends from the first leg 104 toward the second leg 106. A foot 118 extends outwardly from the first flag 114 away from the first and second legs 104, 106. A latch 120 extends upwardly from the foot 118 and is positioned between the legs 104, 106.

During operation of the device, the body 47 of safety assembly 46 is connected the catheter hub 16 where the introducer needle 18 passes through the catheter hub 16 and the body 47. The introducer needle 18 cooperates with the clip 100 by biasing the clip into a locked position by pressing legs 104, 106 of the clip toward one another. The introducer needle 18 contacts the outer surface of the leg 106 to retain the leg 106 in a compressed state with respect to the first leg as shown in FIG. 7. In the locked position, the latch 120 engages the collar 45 on catheter hub 16 to prevent removal of the catheter hub 16 from safety assembly 46. The clip 100 is in a position that allows the introducer needle 18 to slide within the device.

As the needle is withdrawn from the catheter hub and into the safety assembly, the tip of the needle 18 clears the clip 100 and the leg 106 of the clip 100 is allowed to expand outwardly where the second leg 106 moves away from the first leg 106. As the clip 100 expands, the first and second flags 114, 116 block the opening in the body 47 and prevent the tip of the introducer needle 18 from exiting the distal end of the body 47.

Movement of the second leg 106 moves the latch 120 from engagement with the collar 45 of the catheter hub 16 to a position aligned with the opening in the collar. This allows the hub 16 to disengage from the body 47. As the needle 18 is pulled further in the proximal direction, the needle 18 slides through the body 47 until a crimp or deformation 122 formed near the distal end of the needle 18 engages washer 102. The washer 102 has an opening to allow passage of the needle shaft but not the crimp or deformation 122. The opening has an inner dimension less than an outer dimension of the crimp or deformation 122. The washer prevents the distal tip of the needle 18 and the crimp or deformation 122 from exiting the assembly when the needle is retracted. The combination of the clip 100 and washer 102 function as a needle tip protection mechanism to cover the needle tip and prevent a needle stick injury. In other embodiments, other types of safety mechanisms can be used having different shapes and features used on other peripheral IV catheters.

In the embodiment illustrated, a blood flashback feature is provided in the catheter device. Flashback is the visibility of blood that confirms the entry of the needle tip into a vein. Primary flashback can be seen through the catheter tubing 14 as blood travels into the open distal end of the hollow needle 18 and then exits through a notch or opening 126 in the needle 18 near the needle tip as shown in FIG. 7. The blood travels up through the internal annular space between the needle 18 and the inside of the catheter 14. In one embodiment, a secondary flashback can be seen in a needle hub when the blood comes out of the back of the catheter 14 and enters a flash chamber in the needle hub. Air can be vented by a plug in the back of a needle hub or inside the housing by a porous membrane or micro grooves. A tertiary flashback can be seen in the catheter hub when blood from the primary flashback flows into the hub and stops at a blood control septum 48. Air is vented is vented by micro grooves in the periphery of the blood control septum 48. The features described in this embodiment can be used in combination with the features described in this invention.

The above description of the preferred embodiments is not to be deemed as limiting the invention, which is defined by the appended claims. The disclosure is intended to enable the artisan of ordinary skill to practice variants of the invention described without departing from the scope of the invention. Numerical limitations herein, in the specification and in the claims, are understood to be limited by the modifier "about," such that minor departures yielding equivalent results is within the scope of the invention. Features or dependent claim limitations disclosed in connection with one embodiment or independent claim may be combined in another embodiment with a different independent claim without departing from the scope of the invention.

The invention claimed is:

1. A catheter insertion device comprising:
a housing having a longitudinal dimension with a proximal end, a distal end and a cavity extending between said distal end and proximal end, said distal end having an opening;
a catheter extending through said opening of said housing, said catheter having distal end and a proximal end coupled to a catheter hub received in said cavity of said housing and being movable from a first retracted position to a second extended position relative to said housing, said catheter extending from said distal end of said housing;
an introducer needle positioned in said housing, said introducer needle having a proximal end coupled to said housing and a distal end extending through said catheter; and
an actuator assembly including a body in said housing, said body being movable in a longitudinal direction of said housing and operatively connected to said catheter and catheter hub, said body being movable from a first position to a second position toward said distal end of said housing to move said catheter hub and catheter over said introducer needle toward said distal end of said housing and said distal end of said introducer needle, and said actuator assembly is configured to prevent said catheter hub and catheter from movement toward said proximal end of said housing when an actuator body moves toward said proximal end of said housing.

2. The catheter insertion device of claim 1, wherein said actuator assembly includes an actuator button for sliding said body within said housing.

3. The catheter insertion device of claim 2, wherein said body is coupled to said catheter hub and separable from said catheter hub, and said actuator assembly includes said actuator body operatively connected to said body for sliding said body within said housing.

4. The catheter insertion device of claim 3, wherein said actuator body includes at least one tab for sliding over said body in a direction toward said proximal end of said housing, and where said at least one tab engages said body to slide said body in a direction toward said distal end of said housing.

5. The catheter insertion device of claim 3, wherein said actuator body includes an indexing assembly configured for moving said body toward said distal end of said housing and preventing sliding movement of said body toward proximal end of said housing.

6. The catheter insertion device of claim 5, wherein said housing includes an indexing assembly configured to enable movement of said body toward said distal end of said housing and preventing sliding movement of said body toward said proximal end of said housing.

7. The catheter insertion device of claim 3, wherein said actuator body includes a plurality of spaced-apart flexible tabs for engaging a complementing surface on said body and sliding said body toward said distal end of said housing by sliding movement of said actuator body toward distal end of said housing.

8. The catheter insertion device of claim 7, wherein said housing includes a plurality of spaced-apart flexible tabs for engaging a complementing surface on said body allowing sliding of said body toward said distal end of said housing and preventing sliding of said body toward said proximal end of said housing.

9. The catheter insertion device of claim 3, wherein said body is a needle safety assembly having a spring clip for blocking a distal opening in said body when said introducer needle is withdrawn from said catheter, and a washer to prevent separation of said introducer needle from said body.

10. A catheter insertion device comprising:
a housing having a proximal end, a distal end, and a cavity extending between said distal end and proximal end;
a catheter having a catheter hub received in said cavity of said housing and being movable from a first retracted position to a second extended position relative to said housing, said catheter extending from said distal end of said housing;
an introducer needle positioned in said housing, said introducer needle having a proximal end coupled to said housing and a distal end extending through said catheter;
a body having a proximal end, and a distal end coupled to said catheter hub, said body being movable in a longitudinal direction of said housing toward said distal end and configured to prevent said body from moving toward said proximal end of said housing; and
an actuator body coupled to said housing and to said body, said actuator body being movable from a first position to a second position to move said body and catheter hub toward said distal end of said housing and movable from said second position toward said proximal end of said housing.

11. The catheter insertion device of claim 10, wherein said actuator body includes an indexing mechanism configured to allow sliding movement of said body toward said distal end and resisting movement of said body toward said proximal end.

12. The catheter insertion device of claim 10, wherein said housing includes an indexing mechanism configured to allow sliding movement of said body toward said distal end of said housing and resisting movement of said body toward said proximal end.

13. The catheter insertion device of claim 11, wherein said actuator body is connected to an actuator button for sliding said actuator body within said housing.

14. The catheter insertion device of claim 10, wherein said body is separable from said catheter hub and said catheter.

15. The catheter insertion device of claim 10, wherein said actuator body includes at least one first tab for sliding over said body in a direction toward said proximal end of said housing and where said at least one tab engages said body to slide said body in a direction toward said distal end of said housing when said actuator body slides toward said distal end of said housing.

16. The catheter insertion device of claim 15, further comprising at least one second tab for engaging said body and resisting sliding movement of said body toward said proximal end of said housing.

17. The catheter insertion device of claim 16, wherein said at least one second tab is coupled to said housing.

18. The catheter insertion device of claim 16, wherein said actuator body includes a plurality of said first tabs for engaging a complementing surface on the body for sliding said body toward said distal end of said housing in a step-wise manner by sliding movement of said actuator body toward distal end of said housing.

19. The catheter insertion device of claim 18, further comprising a plurality of said second tabs extending from said housing for engaging said body and allowing sliding of said body toward said distal end of said housing and preventing sliding of said body toward said proximal end of said housing.

20. The catheter insertion device of claim 10, wherein said body includes a spring clip for blocking an opening in said body when said introducer needle is withdrawn from said catheter, and a washer to prevent separation of said introducer needle from said body.

21. A catheter insertion device comprising:
   a housing having proximal end, a distal end, and a cavity extending between said distal end and proximal end;
   a catheter having a catheter hub received in said cavity of said housing and being movable from a first retracted position to a second extended position relative to said housing, said catheter extending from said distal end of said housing;
   an introducer needle positioned in said cavity of said housing, said introducer needle having a proximal end coupled to said housing and a distal end extending through said catheter;
   a body having a proximal end, and a distal end coupled to said hub, said body being movable in a longitudinal direction of said housing toward said distal end and being prevented from moving toward said proximal end of said housing;
   an actuator body coupled to said housing and being movable from a first position to a second position to slide within said housing, said actuator body having a ratcheting mechanism for engaging said body to move said body and catheter hub toward said distal end of said housing; and
   said housing having a ratcheting mechanism for engaging said body allowing movement of said body toward said distal end of said housing and resisting movement of said body toward said proximal end of said housing when said actuator body moves toward said proximal end of said housing.

22. The catheter insertion device of claim 21, wherein said ratcheting mechanism of said actuator body comprises a plurality of flexible first tabs on said actuator body projecting at an incline toward said distal end of said housing for engaging said body to move said body toward said distal end when said actuator body slides toward said distal end.

23. The catheter insertion device of claim 22, wherein said ratcheting mechanism of said housing comprises a plurality of flexible second tabs on said housing projecting at an incline toward said distal end of said housing, said plurality of flexible second tabs enabling said body to move toward said distal end of said housing and resist movement of said body toward said proximal end of said housing.

* * * * *